United States Patent [19]

Heinzerling

[11] Patent Number: 4,564,171
[45] Date of Patent: Jan. 14, 1986

[54] FLOW REGULATOR FOR SETTING AND MAINTAINING A CONSTANT FLOW OF BLOOD, BLOOD-SUBSTITUTE, OR SIMILAR LIQUID

[75] Inventor: Walter C. Heinzerling, Malsfeld Beiseförth, Fed. Rep. of Germany

[73] Assignee: Infusionstechnik Clinico GmbH & Co., Bad Hersfeld, Fed. Rep. of Germany

[21] Appl. No.: 720,060

[22] Filed: Apr. 8, 1985

Related U.S. Application Data

[63] Continuation of Ser. No. 542,366, Oct. 17, 1983, abandoned.

[30] Foreign Application Priority Data

Apr. 19, 1983 [DE] Fed. Rep. of Germany ... 8311508[U]

[51] Int. Cl.$^4$ .............................................. F16K 5/04
[52] U.S. Cl. .................................. 251/209; 251/205; 251/309
[58] Field of Search ............. 251/205, 208, 209, 215, 251/309, 312, 318, 319, 324

[56] References Cited

U.S. PATENT DOCUMENTS

| | | | |
|---|---|---|---|
| 3,255,775 | 6/1966 | Albro et al. | 251/215 |
| 3,490,736 | 1/1970 | Snyder | 251/215 |
| 3,747,894 | 7/1973 | Pepper | 251/215 |
| 3,910,553 | 10/1975 | Boylan | 251/205 |
| 4,147,184 | 4/1979 | Jess | 251/312 |
| 4,262,880 | 4/1981 | Danko et al. | 251/209 |
| 4,408,745 | 10/1983 | Swiers et al. | 251/215 |

FOREIGN PATENT DOCUMENTS

| | | | |
|---|---|---|---|
| 550214 | 8/1956 | Belgium | 251/205 |
| 951789 | 10/1956 | Fed. Rep. of Germany | 251/208 |
| 1033980 | 7/1958 | Fed. Rep. of Germany | 251/209 |
| 1129686 | 8/1956 | France | 251/209 |
| 1189277 | 3/1959 | France | 251/215 |
| 1315665 | 5/1973 | United Kingdom | 251/215 |

*Primary Examiner*—Samuel Scott
*Assistant Examiner*—Noah Kamen
*Attorney, Agent, or Firm*—Max Fogiel

[57] ABSTRACT

Flow regulator for setting and maintaining a constant flow of blood, blood-substitute, or similar liquid and consisting of a body with a movable part mounted on it and having, first, a bore that serves as a valve housing and accepts the movable part, which serves as a plug, and, second, two connections that communicate more or less at right angles with the bore and have perforations for a flow line and in that the axes of the connections or of their perforations are mutually displaced along the body in such a way that the plug can move in the valve housing only in the vicinity of one perforation from a position allowing complete access to a position ensuring complete closure.

7 Claims, 3 Drawing Figures

FLOW REGULATOR FOR SETTING AND MAINTAINING A CONSTANT FLOW OF BLOOD, BLOOD-SUBSTITUTE, OR SIMILAR LIQUID

This application is a continuation of Ser. No. 542,366 filed Oct. 17, 1983, now abandoned.

BACKGROUND OF THE INVENTION

The present invention relates to a flow regulator for setting and maintaining a constant flow of blood, blood-substitute, or similar liquid and consisting of a body with a movable part mounted on it. Flow regulators of this type are employed in medical technology in particular, where it is important to set and maintain a constant flow even when the volume is very small, when the liquid is in drops for example, and must be individually set and maintained constant over a particular period—the total infusion or transfusion time.

A flow regulator of this type in the form of a compression-roller device that squeezes a flexible tube to a greater or lesser extent to vary its flow diameter is known. The device has a body through which the tube is fed. A movable, wheel-like part with axle stubs projecting from each side slides in a guide slot on the body. The guide slot is associated with a slanting plane on the body in such a way that the tubing can be squeezed to a greater or lesser extent between the movable part and the slanting plane and retained in the squeezed state. The drawback to this known flow regulator is that it does not allow the number of drops to be adjusted precisely over a long period because choking the flow with the movable roller exerts pressure on the tube and plastically preforms it more or less permanently. The elasticity and change in shape of the tube and swelling phenomena in its material will alter the preset number of drops after a while and will as is known require, often several, readjustments. Another disadvantage of the known device is that the flow cross-section of the tube narrows into more or less of a slit after a long period of administration at a low drop number, affecting the resiliency of the tube and preventing the subsequent setting of a desired higher flow. The larger volume can be administered to the patient only by replacing the tube or by other means.

SUMMARY OF THE INVENTION

The object of the present invention is an improved flow regulator of the aforesaid type that allows setting a constant flow with comparatively greater precision so that a constant drop number can be set and maintained over the whole period of administration even when the flow is very low.

This object is attained in accordance with the invention in that the body has, first, a bore that serves as a valve housing and accepts the movable part, which serves as a plug, and, second, two connections that communicate more or less at right angles with the bore and have perforations for a flow line and in that the axes of the connections or of their perforations are mutually displaced along the body in such a way that the plug can move in the valve housing only in the vicinity of one perforation from a position allowing complete access to a position ensuring complete closure. One advantage is that the blood is treated very gently because only one perforation is opened to a greater or lesser extent to establish a constant flow. Another advantage is that the parts are stable castings, avoiding the drawbacks that result from diminished elasticity. The flow regulator is nevertheless very simple in design and inexpensive to manufacture.

The body can have a T-shaped cross-section with the movable part overlapping the wall of the bore toward the outside and having knurls, corrugations, or similar structures on the outside to facilitate rotating it to adjust the flow. Thus, the body forms a T connector, although with the axes of the connections or perforations that communicate with the valve housing mutually displaced.

The movable part can be attached to the body with a continuous rib-and-groove connection and can rotate on the body, with a slanting plane on the front of the extension that projects into the bore to more or less block off one perforation when the movable part is rotated. The continuous rib-and-groove connection allows the movable part to rotate while preventing it from moving axially. It is accordingly necessary for the extension of the movable part to terminate in a slanting plane that will more or less block off or open up the one perforation in accordance with the angle of rotation of the movable part relative to the body.

In another embodiment of the flow regulator the movable part is threaded onto the body and the front of the extention that projects into the bore has a closure edge. This closure edge specifically extends at a right angle and hence around the axis of the movable part. The threading allows the movable part not only to rotate but also to move axially in relation to the body. The closure edge and the adjacent wall of the extension can accordingly cover the perforation to a greater or lesser extent, facilitating a precise and reliable adjustment of the number of drops over the desired period.

It is practical for the body and movable part to be injection-molded plastic parts with a fixed shape that does not exploit the resiliency of the material. A seal can be obtained between the movable part and the body by appropriately matching their shapes or by inserting a gasket made out of an elastomeric material.

BRIEF DESCRIPTION OF THE DRAWINGS

Two preferred embodiments of the invention will now be described by way of example with reference to the attached drawings, wherein.

DESCRIPTION OF THE PREFERRED EMBODIMENTS

Figure 1:
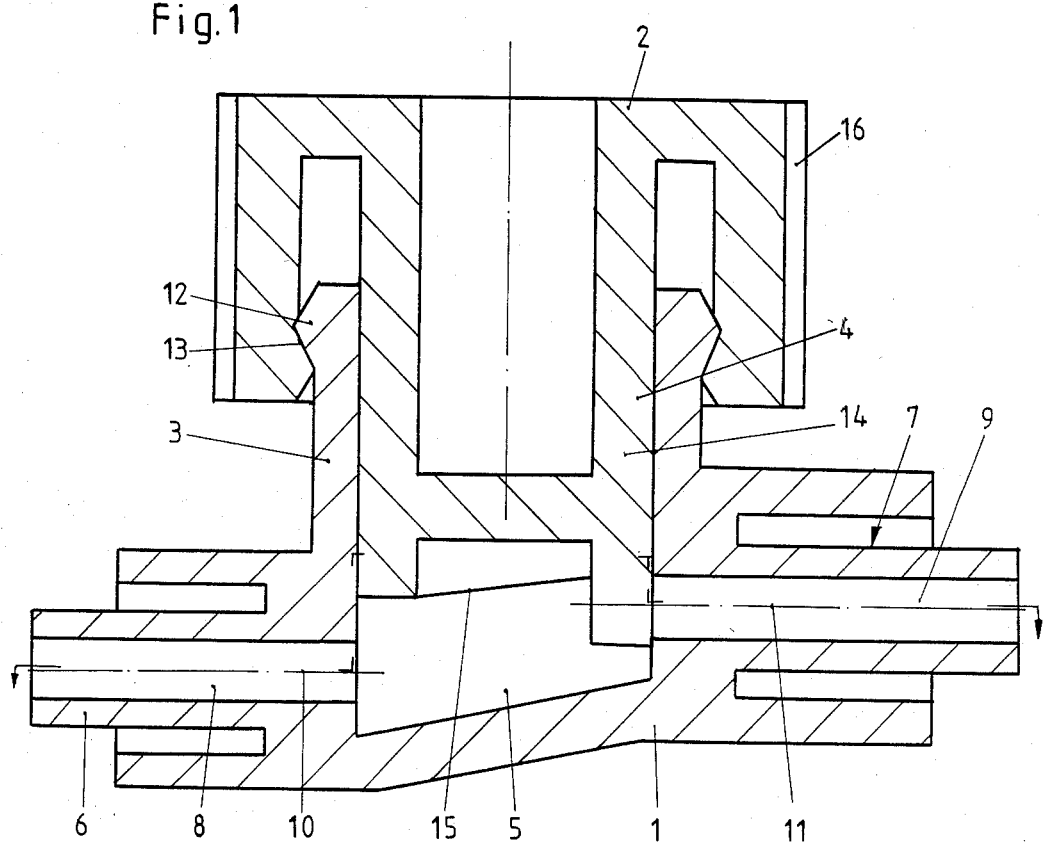
FIG. 1 is a vertical section through one embodiment of a flow regulator in accordance with the invention.
Figure 2:
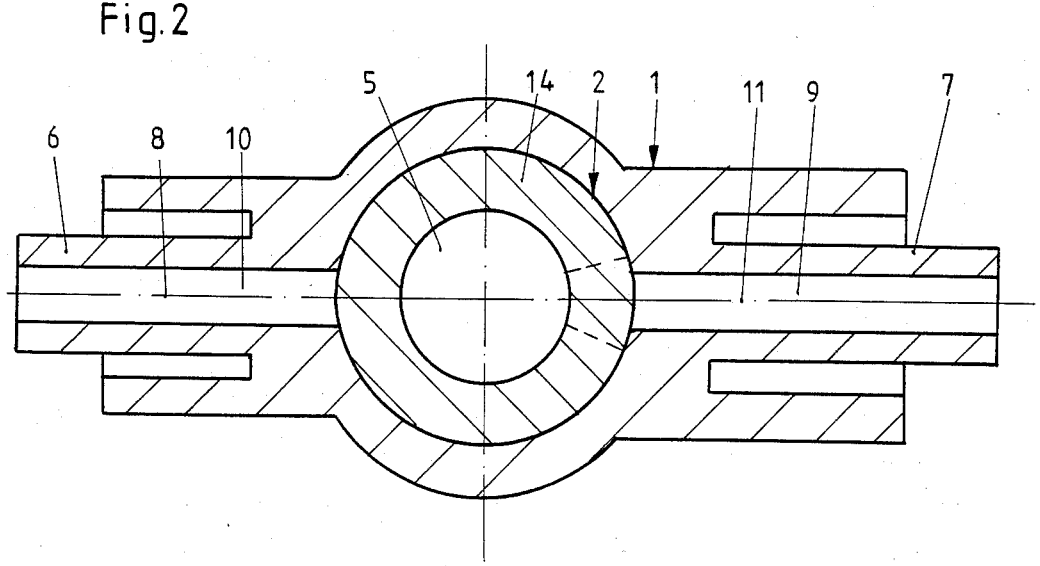
FIG. 2 is a section along line II—II in FIG. 1.

The flow regulator consists essentially of two components, one a body 1 and the other a movable part 2. Body 1 is a T connector with a bore 4 through its wall 3. Bore 4 terminates in a valve housing 5. Body 1 also has two connections 6 and 7 with perforations 8 and 9 respectively that communicated with valve housing 5. The axes 10 and 11 of perforations 8 and 9 respectively are, as will be evident from FIG. 1, mutually displaced. Connections 6 and 7 fit on sections of the type of tubing or line that is conventionally employed in medicine.

Body 1 has a continuous rib 12 at the end of its wall 3 that operates in conjunction with a continuous groove 13 on movable part 2 in such a way that part 2 can be snapped over and will rotate on wall 3. Part 2 has an extension 14 that projects into bore 4 and, in the embodiment illustrated in FIG. 1, terminates in a slanting plane 15 that continues around most of the circumference of the extension. Only about half of plane 15 is shown in FIG. 1. Extension 14 and plane 15 are designed and positioned so that a simple rotation of movable part 2 will more or less completely separate the perforation 9 in connection 7 from valve housing 5. The perforation 8 in connection 6, however, will always remain in complete communication with housing 5. Rotating movable part 2 will, as is evident, always set and maintain a constant flow or number of drops of liquid through the regulator. Movable part 2 has knurls or corrugations 16 on the outside to facilitate operation. It may also be provided with wings or have a polygonal shape.

Extension 14 fits into the bore 4 in body 1 precisely enough to produce a proper seal.

Figure 3:
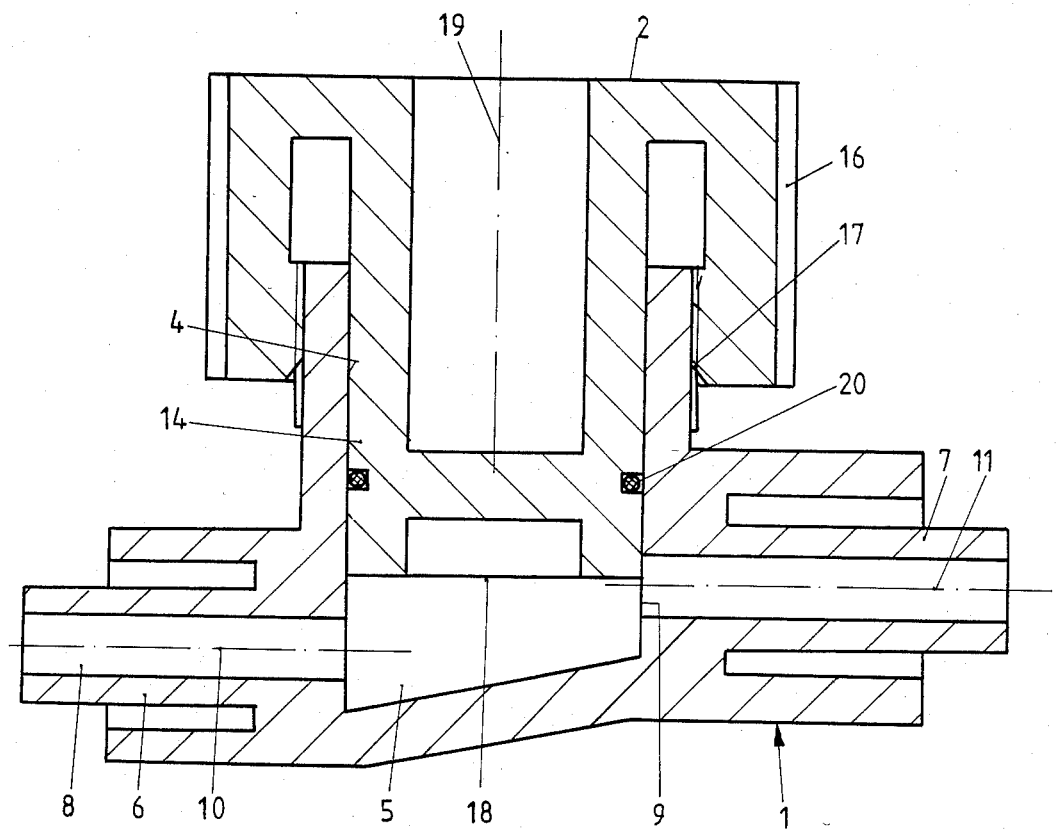
FIG. 3 is a vertical section through another embodiment of the invention.

FIG. 3 illustrates another embodiment in which movable part 2 is attached to body 1 with threads 17 in such a way that rotating the part will also displace it axially within bore 4. In this embodiment extension 14 terminates within bore 4 or valve housing 5 in a continuous closure edge 18 that extends at all points at a right angle to the axis 19 of part 2. Extension 14 also has a seal 20. It will be evident that this embodiment also allows particularly precise adjustment of the flow or number of drops by rotating part 2 in relation to body 1. Only perforation 9 through connection 7 is more or less closed off or opened up in this case as well.

I claim:

1. Flow regulator for setting and maintaining a constant flow of blood-substitute, or similar liquid, comprising: a main member having a bore; a movable part mounted on said main member and serving as a closure element; a valve chamber forming said bore and having two connections communicating substantially perpendicular to an axis of said bore and having ducts for a flow line; said connections having axes displaced relative to each other in said chamber so that the closure element in said valve chamber can move only in the vicinity of one duct from a complete open position to a completely closed position; said flow line being fully blocked in said closed position, flow through said movable part being free of flow resistance when in said open position, said ducts being displaced relative to each other so that said movable part leaves said ducts fully uncovered when in said open position for unthrottled flow though the flow regulator, said ducts having substantially parallel axes, a passage surface being present for blood flow when said flow regulator is substantially half closed, said surface comprising substantially a sector of a circular surface having a length and width substantially equally large, one of said ducts forming also a valve seat; an extension projecting into said bore, said main member being formed of a substantially 360° incline on said extension, said incline having a circular shape dependent on a position of free passage cross-section of said duct and substantially blocking off said duct at partial settings of said flow regulator, blood through said flow regulator having minimum deflections and minimum change in direction of flow.

2. Flow regulator as defined in claim 1, wherein said main member has a T-shaped cross-section, said movable part overlapping a wall of said bore toward the outside and having knurl-shaped means on the outside.

3. Flow regulator as defined in claim 1, wherein said movable part is attached to said main member with a continuous rib-and-groove connection and rotates on said main member, a slanting plane surface on front of an extension projecting into said bore to substantially block off one perforation when said movable part is rotated.

4. Flow regulator as defined in claim 1, wherein said movable part is attached to said main member with threads, and extension means projecting into said bore and having a front portion with a closure edge.

5. Flow regulator as defined in claim 3, wherein said main member and movable part are injection-molded plastic parts.

6. Flow regulator as in claim 3, and seal means between said movable part and said main member.

7. Flow regulator for setting and maintaining a constant flow of blood-substitute, or similar liquid, comprising: a main member having a bore; a movable part mounted on said main member and serving as a closure element; a valve chamber forming said bore and having two connections communicating substantially perpendicular to an axis of said bore and having ducts for a flow line; said connections having axes displaced relative to each other in said chamber so that the closure element in said valve chamber can move only in the vicinity of one duct from a complete open position to a completely closed position; said flow line being fully blocked in said closed position, flow through said movable part being free of flow resistance when in said open position, said ducts being displaced relative to each other so that said movable part leaves said ducts fully uncovered when in said open position for unthrottled flow through the flow regulator, said ducts having substantially parallel axes; said main member having a T-shaped cross-section, said movable part overlapping a wall of said bore toward the outside and having knurl-shaped means on the outside; said movable part being attached to said main member with a continuous rib-and-groove connection and rotating on said main member, a slanting plane surface on front of an extension projecting into said bore to substantially block off one perforation when said movable part is rotated; said main member and movable part being injection-molded plastic parts; and seal means betwen said movable part and said main member, a passage surface being present for blood flow when said flow regulator is substantially half closed, said surface comprising substantially a sector of a circular surface having a length and width substantially equally large, one of said ducts forming also a valve seat; an extension projecting into said bore, said main member being formed of a substantially 360° incline on said extension, said incline having a circular shape dependent on a position of free passage cross-section of said duct and substantially blocking off said duct at partial settings of said flow regulator, blood through said flow regulator having minimum deflections and minimum change in direction of flow.

* * * * *